United States Patent [19]
Bredeweg et al.

[11] Patent Number: 5,368,725
[45] Date of Patent: Nov. 29, 1994

[54] APPARATUS FOR STOP FLOW MEMBRANE PROBE ANALYSIS

[75] Inventors: Robert A. Bredeweg; Engin D. Yalvac, both of Midland, Mich.

[73] Assignee: The Dow Chemical Company, Midland, Mich.

[21] Appl. No.: 998,112

[22] Filed: Dec. 29, 1992

[51] Int. Cl.$^5$ .............................................. B01D 65/00
[52] U.S. Cl. .................................. 210/137; 210/195.2; 210/257.2; 210/511; 422/69; 422/101; 422/103
[58] Field of Search ............... 210/640, 641, 643, 644, 210/650, 656, 659, 195.2, 198.2, 248, 257.2, 321.65, 744, 110, 109; 422/69, 70, 100, 101, 103; 436/178; 73/863.23; 250/188, 188 A; 137/590.5

[56] References Cited

U.S. PATENT DOCUMENTS

| | | | |
|---|---|---|---|
| 4,529,521 | 7/1985 | Cortes et al. | 210/635 |
| 4,751,004 | 6/1988 | Stevens et al. | 210/659 |
| 4,775,476 | 10/1988 | Melcher et al. | 210/635 |
| 4,791,291 | 12/1988 | Tou | 250/288 A |
| 4,791,292 | 12/1988 | Cooks et al. | 250/288 |
| 4,837,161 | 6/1989 | Stevens et al. | 436/52 |
| 4,913,821 | 4/1990 | Melcher et al. | 210/635 |
| 4,962,042 | 10/1990 | Morabito et al. | 436/161 |
| 5,124,042 | 6/1992 | Bredeweg et al. | 436/151 |

FOREIGN PATENT DOCUMENTS 9215012 9/1992 European Pat. Off. .
60-22068 1/1987 Japan .................................. 137/590.5

Primary Examiner—Joseph W. Drodge
Attorney, Agent, or Firm—Timothy S. Stevens

[57] ABSTRACT

Apparatus for stop flow membrane probe analysis which apparatus is especially suitable for on-line analysis, the apparatus necessarily including five parts. The first part is a reservoir for containing an extractant. The second part is a flow control unit, being a pump or valve, the flow control unit connected to the reservoir, the flow control unit being of the type that can be turned on and off. The third part is a flow through membrane probe, the flow through membrane probe being connected to the flow control unit. The fourth part is a detector, the detector being connected to the flow through membrane probe. The fifth part is a switch for turning the flow control unit on and off so that the apparatus can be used for stop flow analysis. Preferably, the detector is also connected with the reservoir so that the extractant flowing through the probe and detector can be. recycled back to the reservoir. The probe is immersed into a process stream. A component of interest of the process stream permeates across the membrane into the extractant to be detected by the detector.

2 Claims, 2 Drawing Sheets

APPARATUS FOR STOP FLOW MEMBRANE PROBE ANALYSIS

BACKGROUND

Membranes have been widely used in chemical analysis. Cortes and Davis, U.S. Pat. No. 4,529,521, used membranes to determine components of interest in latex serum. Stevens, Jewett and Bredeweg, U.S. Pat. No. 4,751,004 used membranes to suppress an Ion Chromatography eluent. Morabito, Melcher, Hiller and McCabe, U.S. Pat. No. 4,962,042 used membranes in a Gas Chromatography system. Stevens, Frawley, Swart, Harris, Diedering, Nicholson and Rothman, U.S. Pat. No. 4,837,161, used membranes to add reagent to a Flow Injection Analysis carrier stream. Melcher and Burr, U.S. Pat. No. 4,913,821, used membranes in a phenol analyzer. Melcher and Cortes, U.S. Pat. No. 4,775,476 described a Liquid Chromatography system employing a membrane, the membrane partitioning a sample from a flowing stream of an extractant, a component of interest permeating across the membrane from the sample into the extractant. Melcher and Cortes also described that the flow of the extractant could be stopped to increase the concentration of the component of interest in the extractant. Yalvac, Melcher and Bredeweg, PCT International Publication Number WO 92/15012, used membranes to determine organic acids. Flow through membrane probes are known in the art of membrane chemical analysis.

The apparatus used in membrane chemical analysis systems typically includes a number of valves. However, when a membrane chemical analysis system is used to analyze a chemical process stream and is installed in the process area, i.e., on-line analysis, then the valves can require more maintenance than is desired especially if the valves are multiport valves. It would be an advance in the art of membrane chemical analyzers if the number and complexity of the valves used could be reduced.

SUMMARY OF THE INVENTION

The instant invention is apparatus for stop flow membrane probe analysis which is especially suitable for on-line analysis. No filtration of the process stream to be analyzed is needed. In one embodiment, no valves are needed. In another embodiment only one simple valve is needed.

One embodiment of the instant invention comprises five elements. The first element is a reservoir for containing an extractant. The second element is a pump, the pump being in liquid communication with the reservoir, the pump being of the type that can be turned on and off. The third element is a flow through membrane probe, the flow through membrane probe being in liquid communication with the pump. The fourth element is a detector, the detector being in liquid communication with the flow through membrane probe. The last element is a means for turning the pump on and off so that the apparatus can be used for stop flow analysis. Preferably, the detector is also in liquid communication with the reservoir so that an extractant contained in the reservoir can be recycled.

Another embodiment of the instant invention comprises five elements. The first element is a reservoir for containing an extractant. The second element is a valve, the valve being in liquid communication with the reservoir, the valve being of the type that can be turned on and off. The third element is a flow through membrane probe, the flow through membrane probe being in liquid communication with the valve. The fourth element is a detector, the detector being in liquid communication with the flow through membrane probe, the detector being positioned below the reservoir so that an extractant contained in the reservoir flows through the valve, the flow through membrane probe and the detector by gravity flow. The last element is means for turning the valve on and off so that the apparatus can be used for stop flow analysis. This embodiment can further include a container for containing an extractant, the container being in liquid communication with the detector, the container being positioned below the reservoir so that an extractant contained in the reservoir flows through the valve, the flow through membrane probe, the detector and into the container by gravity flow and a pump, the pump being in liquid communication with the container and the reservoir so that an extractant contained in the reservoir and in the container can be recycled between the reservoir and the container. In addition, this embodiment can yet further include means for controlling the level of an extractant contained in the reservoir such as an overflow conduit, the overflow conduit being in liquid communication with the reservoir and the container, the overflow conduit connected to the reservoir at that position of the reservoir where it is desired to control the level of an extractant contained in the reservoir.

DETAILED DESCRIPTION OF THE INVENTION

Figure 1:
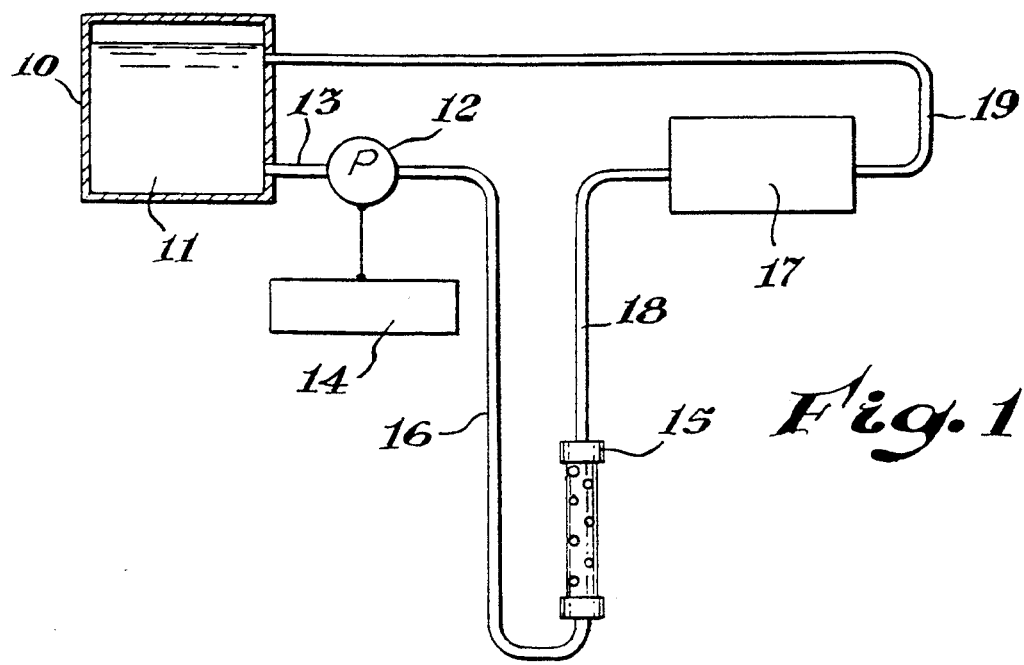
FIG. 1 is a schematic drawing of one embodiment of the instant invention including a flow through membrane probe.

Referring now to FIG. 1, therein is shown one embodiment of the instant invention including a reservoir 10. The reservoir 10 is provided to contain a liquid extractant 11. A Pump 12 is in liquid communication with the reservoir 10 by a first tube 13. The pump 12 is of the type that can be turned on and off such as a pump that is powered by an electric motor. A means 14 for turning on and off the pump 12 is provided such as a means for turning on and off the electricity to a pump that is powered by an electric motor.

A flow through membrane probe 15 is in liquid communication with the pump 12 by a second tube 16. A flow through membrane probe is defined by a semipermeable membrane which partitions a flow channel from an exposed surface of the membrane. The extractant 11 is flowed through the flow channel while the exposed surface of the membrane is contacted with a process stream by immersing the probe into the process stream. A component of interest of the process stream permeates across the membrane and into the extractant 11.

The flow through membrane probe 15 can take many forms. For example the membrane can be in the form of a sheet or sheets or the membrane can be in the form of a tube or tubes. A tubular membrane is preferred since the flow channel can be the bore of the tubular membrane. A specific flow through membrane probe will be discussed below in detail in reference to FIG. 3.

The use of a flow through membrane probe in the instant invention is an advance over the flow through membrane cell used for example by Yalvac, Melcher and Bredeweg as published in PCT International Publication Number WO 92/15012 because there is no need to filter the process stream if it contains objectionable particulates.

Referring still to FIG. 1, a detector 17 is in liquid communication with the probe 15 by a third tube 18. The purpose of the detector 17 is to detect the component of interest of the process stream that permeated across the membrane and into the extractant flowing through the probe 15. The detector 17 must be of a type that detects, directly or indirectly, the component of interest in the extractant 11. The extractant 11 may contain a reagent that improves or causes the component of interest to be detected as is well known in the art. Specific examples of suitable detectors include the electrochemical, conductimetric and spectroscopic detectors that are used in liquid chromatography.

The detector can be combined with the probe and such combinations are intended herein to be within the scope of the term "the detector being in liquid communication with the flow through membrane probe". For example, optical fibers from the detector can be used to direct light into and away from the probe. In another approach, a light emitting diode and a photodiode can be immersed into the flow channel of the probe. Alternatively, a diode laser and a photodiode can be immersed into the flow channel of the probe.

A fourth tube 19 is used to recycle the extractant 11 back to its reservoir 10. The use of the fourth tube 19 is optional in the instant invention. However, the use of the fourth tube 19 greatly reduces the quantity of extractant 11 that needs to be prepared for use in the instant invention.

When the probe 15 is immersed into a process stream containing a component of interest which permeates across the membrane and into the extractant 11, then the detector 17 senses the component of interest at a concentration which is dependent on the flow rate of the extractant 11 flowing through the probe 15.

When the means 14 for turning on and off the pump 12 is used to turn off the pump 12, then the flow of extractant 11 through the probe 15 stops. When the flow of extractant 11 through the probe 15 stops, then the concentration of the component of interest in the extractant 11 within the flow channel of the probe 15 increases relative to the concentration of the component of interest in the extractant 11 when the extractant 11 is flowing through the probe 15.

When the means 14 for turning on and off the pump 12 is used to again turn on the pump 12, then the flow of extractant 11 through the probe 15 resumes and the extractant 11 within the flow channel of the probe 15 which contained the increased concentration of the component of interest is flowed through the detector 17 and back to the reservoir 10.

When the extractant 11 which contains the increased concentration of the component of interest flows through the detector 17, then the detector 17 detects this temporarily increased concentration. If strip chart recorder is connected to the detector 17, this temporarily increased concentration will be shown as a peak similar to a chromatographic peak. The size of this peak is a function of the concentration of the component of interest in the process stream and the degree to which the extractant 11 has been recycled. When the concentration of the component of interest builds up to an objectionable level in the recycled extractant, then it should be replaced with fresh extractant. The primary benefit of the apparatus embodiment shown in FIG. 1 is that it uses no valves.

Figure 2:
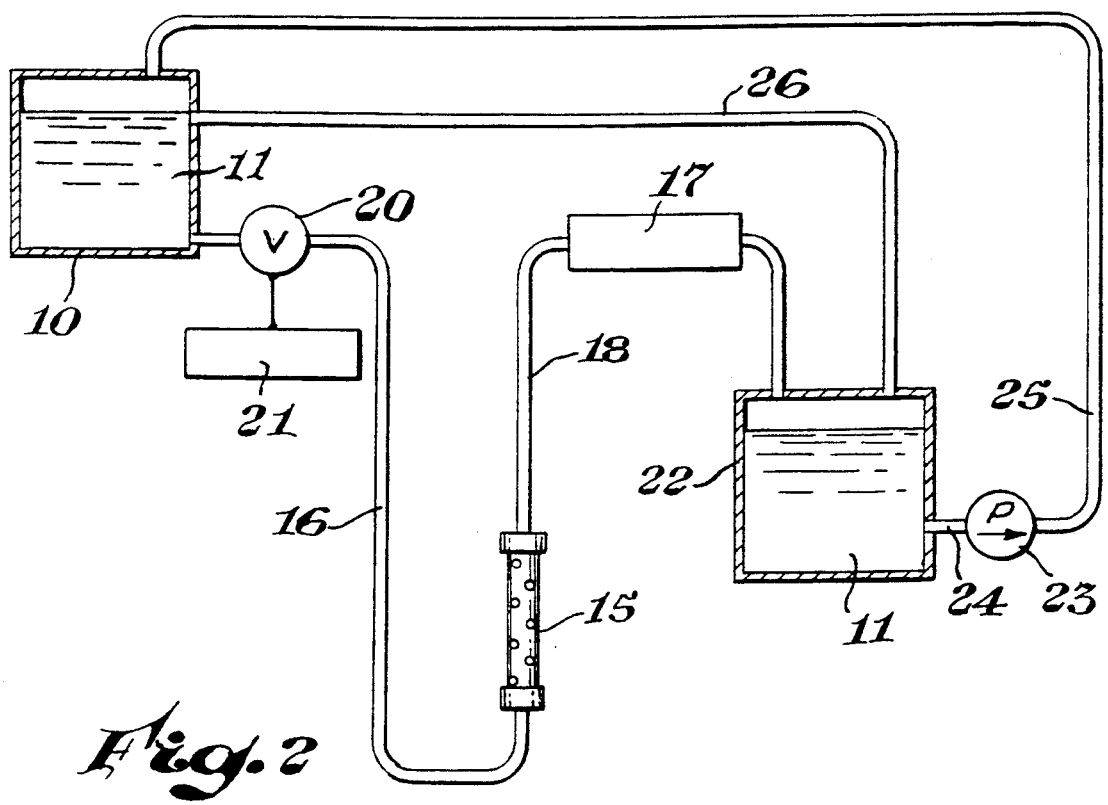
FIG. 2 is a schematic drawing of another embodiment of the instant invention including a flow through membrane probe.

Referring now to FIG. 2, therein is shown another embodiment of the instant invention. Elements of the embodiment shown in FIG. 2 which are the same as the elements shown in FIG. 1 will be referred to by the same reference numbers.

A reservoir 10 is provided to contain a liquid extractant 11. An on/off valve 20 is in liquid communication with the reservoir 10 by a first tube 13. The valve is of the type that can be turned on and off such as a solenoid valve or a compressed air actuated valve. A means 21 for turning on and off the valve 20 is provided such as a means for turning on and off the electricity to a solenoid valve or a means for turning on and off the flow of compressed air to a compressed air actuated valve.

A flow through membrane probe 15 is in liquid communication with the valve 20 by a second tube 16. A detector 17 is in liquid communication with the probe 15 by a third tube 18. The detector 17 is positioned below the reservoir 11 so that the extractant will flow through the valve 20, the probe 15 and the detector 17 by gravity flow.

In FIG. 1 the flow of extractant 11 through the probe 15 is temporarily stopped by temporarily turning off the pump 12. In FIG. 2 the flow of extractant 11 through the probe 15 is temporarily stopped by temporarily turning off the valve 20. Otherwise the operational dynamics of the apparatus of FIG. 1 is essentially the same as the apparatus of FIG. 2.

Preferably, a container 22 is positioned below the reservoir 10 to contain the extractant 11 flowing from the detector 17 and a recycle pump 23 is used to recycle the extractant 11 in the container 22 back to the reservoir 10 by the fifth tube 24 and the sixth tube 25. An overflow conduit 26 is in liquid communication with the container 22 and the reservoir 10 to maintain a constant level of extractant 11 in the reservoir 10. Another means for controlling the level of extractant 11 in the reservoir 10 is to install a float switch in the reservoir 10 and to connect the float switch to the recycle pump 23.

The embodiment shown in FIG. 1 is more preferred than the embodiment shown in FIG. 2 because the embodiment shown in FIG. 1 has no valves. However an important benefit of the embodiment shown in FIG. 2 is that the gravity flow rate is essentially constant which results in a less noisy signal from the detector 17. Another important benefit of the embodiment shown in FIG. 2 is that the recycle pump 23 need not be an expensive precision pump but can be a more inexpensive and perhaps more reliable type of pump.

EXAMPLE 1

Figure 3:
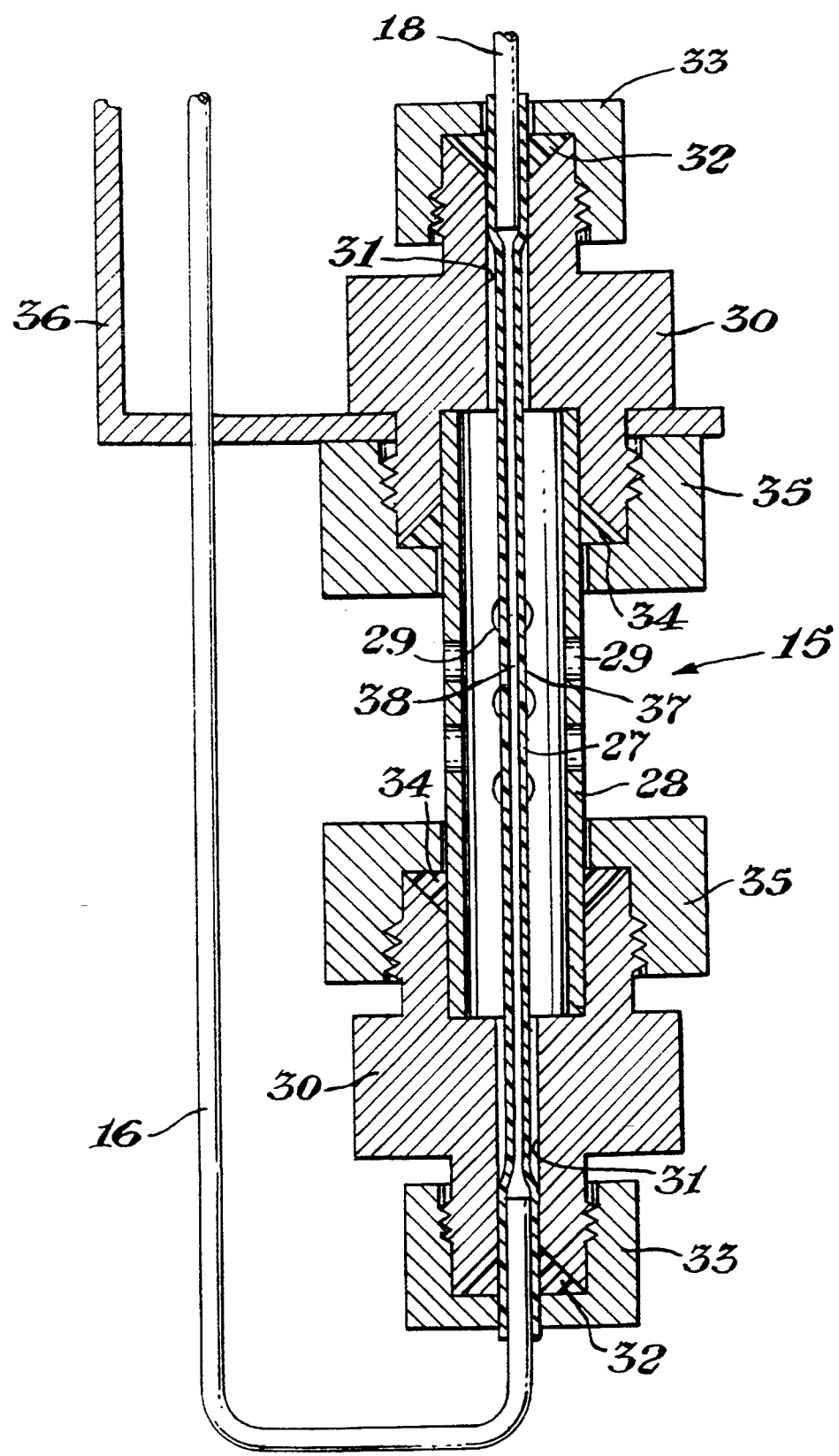
FIG. 3 is a cross-sectional side view of the flow through membrane probe of FIGS. 1 and 2.

This example, among other things, will teach how to make a specific flow through membrane probe for use in the instant invention. Referring now to FIG. 3, therein is shown a cross-sectional side view of the flow through membrane probe 15. The second tube 16 and the third tube 18 are one eighth inch outside diameter stainless steel tubes. The probe 15 includes a single tubular membrane 27 made of silicone rubber (SILASTIC brand silicone rubber tubing, catalog No. 602-235, from Dow Corning Corporation, Midland, Mich.).

The probe 15 includes a perforated shell 28 made from three eights inch outside diameter stainless steel tubing. The shell is perforated with a number of holes 29. A one eighth inch by three eights inch SWAGELOCK brand reducing union 30 is placed at each end of the shell 28. Each union 30 has a minor bore 31 which has been enlarged from its original one eighth inch to a diameter of five thirty seconds of an inch.

A one eighth inch ferrule 32, made of TEFLON brand polymer is drilled out with a five thirty seconds inch drill and tightened onto each union 30 with a one eighth inch nut 33 which has been drilled out with a three sixteenths inch drill. The shell 28 is secured to each union 30 with a three eighths inch stainless steel ferrule 34 and three eights inch nut 35. A bracket 36 is provided to hold the probe 15.

The probe 15 is designed to be immersed into a process stream such as being immersed into a tank containing a chemical process liquid. The holes 29 allow the process liquid to enter the shell 28 and contact an exposed surface 37 of the membrane 27. A component of interest of the process liquid can then permeate across the membrane 27 into a flow channel 38 defined by the bore of the membrane 27. The perforated shell 28 protests the membrane 27 from physical damage.

EXAMPLE 2

This example, among other things, will teach how to make and use the apparatus shown in FIG. 1. The reservoir 10 is a ten liter polyethylene tank. The extractant 11 is 0.1 molar sodium hydroxide solution in water. The pump 12 is a Model M45 liquid chromatography pump from Waters Chromatography Division of Millipore Corporation, Milford, Mass., set to deliver 2.7 milliliters per minute. The probe 15 is described in Example 1 above.

The detector 17 is a Lambda-Max Model 481 UV detector from Waters Chromatography Division of Millipore Corporation and it is set to detect at a wavelength of 280 nanometers. The detector 17 is equipped with a prep-cell having one eighth inch tubes so that the pressure drop across the cell is relatively low since a relatively high pressure drop could burst the membrane of the probe 15.

The detector 17 is connected to a Model 4270 integrator from the Autolab Division of Spectra Physics Corporation, San Jose, Calif. The integrator has a timed event controller which is connected to the pump 12 via a relay to turn the pump 12 on and off.

The integrator is programmed to turn the pump 12 on for ten minutes, off for ten minutes and then on for ten minutes again. The probe 15 is immersed into a series of test solutions containing varying traces of phenol in water and having a pH of about 7. An analysis is performed for each test solution. The integrator records a peak having a maxima about twenty five seconds after the pump 12 is turned on again for each analysis. The integrator records the height of the peaks.

A graph is made of the height of the peaks vs. the concentration of phenol for each test solution. The graph shows a good linear response between 25 parts per million phenol and 500 parts per million phenol.

EXAMPLE 3

This example, among other things, will teach how to make and use the apparatus shown in FIG. 2. The reservoir 10 is a ten liter polyethylene tank. The extractant 11 is 0.1 molar sodium hydroxide solution in water. The container 22 is a ten liter polyethylene tank. The pump 23 is a Model M45 liquid chromatography pump from Waters Chromatography Division of Millipore Corporation, Milford, Mass., set to deliver 5 milliliters per minute. The probe 15 is described in Example 1 above.

The valve 20 is a CHEMINERT brand solenoid valve from the Milton Roy Division of the Laboratory Data Control Corporation. The reservoir 10 is positioned above the container 22 a distance sufficient so that when the valve 20 is on, the extractant 11 flows through the valve 20 at a rate of 2.7 milliliters per minute.

The detector 17 is a Lambda-Max Model 481 UV detector from Waters Chromatography Division of Millipore Corporation and it is set to detect at a wavelength of 280 nanometers. The detector 17 is equipped with a prep-cell having one eighth inch tubes so that the pressure drop across the cell is relatively low since a relatively high pressure drop could burst the membrane of the probe 15.

The detector 17 is connected to a Model 4270 integrator from the Autolab Division of Spectra Physics Corporation, San Jose, Calif. The integrator has a timed event controller which is connected via a relay to the valve 20 to turn the valve on and off.

The integrator is programmed to turn the valve 20 on for ten minutes, off for ten minutes and then on for ten minutes again. The probe 15 is immersed into a series of test solutions containing varying traces of phenol in water and having a pH of about 7. An analysis is performed for each test solution. The integrator records a peak having a maxima about twenty five seconds after the valve 20 is turned on again for each analysis. The integrator records the height of the peaks.

A graph is made of the height of the peaks v. the concentration of phenol for each test solution. The graph shows a good linear response between 25 parts per million phenol and 500 parts per million phenol.

What is claimed is:

1. Apparatus for stop flow membrane probe analysis, the apparatus especially suitable for on-line analysis, the apparatus comprising:
    (a) a reservoir for containing a liquid extractant;
    (b) a valve, the valve being in liquid communication with the reservoir, the valve being of a type that can be turned on and off;
    (c) flow through membrane probe, the flow through membrane probe comprising a semipermeable membrane which partitions a flow channel from an exposed surface of the membrane, the flow channel being in liquid communication with the valve;
    (d) a detector, the detector being in liquid communication with the flow channel of the flow through membrane probe;
    (e) means for turning the valve on and off so that the apparatus can be used for stop flow analysis;
    (f) a container for containing an extractant, the container being in liquid communication with the detector, the container being positioned below the reservoir, the reservoir, valve, membrane, probe, detector and container being constructed and arranged such that an extractant contained in the reservoir flows though the valve, the flow channel of the flow through membrane probe, the detector and into the container in that order by gravity flow;
    (g) a pump, the pump being in liquid communication with the container and the reservoir such that an extractant contained in the container can be recycled into the reservoir; and (h) means for controlling the level of an extractant contained in the reservoir.

2. The apparatus of claim 1, wherein the means for controlling the level of an extractant contained in the reservoir is an overflow conduit, the overflow conduit being in liquid communication with the reservoir and the container and connected to the reservoir.

* * * * *